US006955684B2

(12) United States Patent
Savage, Jr. et al.

(10) Patent No.: US 6,955,684 B2
(45) Date of Patent: Oct. 18, 2005

(54) PORTABLE LIGHT DELIVERY APPARATUS AND METHODS

(76) Inventors: Henry C Savage, Jr., 352 W. 1060 South, Orem, UT (US) 84058; Kent W. Savage, 1489 N. 400 West, American Fork, UT (US) 84003

(*) Notice: Subject to any disclaimer, the term of this patent is extended or adjusted under 35 U.S.C. 154(b) by 0 days.

(21) Appl. No.: 10/113,550

(22) Filed: Mar. 29, 2002

(65) Prior Publication Data

US 2003/0187486 A1   Oct. 2, 2003

(51) Int. Cl.⁷ .................................. A61N 5/01
(52) U.S. Cl. ........................ 607/88; 607/89
(58) Field of Search ................. 607/88–91; 606/9

(56) References Cited

U.S. PATENT DOCUMENTS

| | | | | |
|---|---|---|---|---|
| 5,358,503 A | * | 10/1994 | Bertwell et al. | 606/27 |
| 5,616,140 A | * | 4/1997 | Prescott | 606/10 |
| 5,957,960 A | * | 9/1999 | Chen et al. | 607/92 |
| 6,045,575 A | * | 4/2000 | Rosen et al. | 607/88 |
| 6,063,108 A | * | 5/2000 | Salansky et al. | 607/89 |
| 6,096,066 A | * | 8/2000 | Chen et al. | 607/88 |
| 6,238,425 B1 | * | 5/2001 | Thiberg | 607/88 |
| 6,350,275 B1 | * | 2/2002 | Vreman et al. | 607/88 |
| 6,443,978 B1 | * | 9/2002 | Zharov | 607/91 |
| 6,471,716 B1 | * | 10/2002 | Pecukonis | 607/89 |
| 6,596,016 B1 | * | 7/2003 | Vreman et al. | 607/88 |

* cited by examiner

Primary Examiner—Roy D. Gibson
Assistant Examiner—Henry M Johnson, III
(74) Attorney, Agent, or Firm—TraskBritt, PC

(57) ABSTRACT

A portable light delivery device for delivering light to the blood supply of a human body through a nonocular area of skin on the body includes an attachment member, a portable light delivery unit connected to the attachment member and a portable power supply. The portable light delivery unit provides one or more wavelengths of light within a specifically determined range of intensity and a specifically determined angle of illumination. A portable control unit may be included on the light delivery device for selectively controlling the light delivery unit. A programming device associated with the control unit selectively changes the programming of the controller. The light delivery device is portably secured to a region of the body having a substantial amount of blood vessels near the surface thereof to deliver light to the blood supply of the body for treating mood disorders, seasonal affective disorder and disorders involving circadian rhythm and sleep.

35 Claims, 5 Drawing Sheets

PORTABLE LIGHT DELIVERY APPARATUS AND METHODS

GOVERNMENT RIGHTS

This invention was made with Government support under Contract Nos. N43-NS82393 and MH61043-01, both awarded by the National Institute of Health. The Government has certain rights in this invention.

BACKGROUND OF THE INVENTION

1. Field of the Invention

This invention relates to means for delivering light to the blood supply of a human body to treat mood disorders and sleep and body cycle problems in humans. More particularly, the present invention concerns a portable and wearable light source apparatus, and methods related thereto, for delivering light to the blood supply by exposing a nonocular portion of the body to light in preselected wavelengths for preselected periods of time at optimal times of the day.

2. The Related Art

Seasonal affective disorder (SAD) is a form of recurrent depressive or bipolar disorder that seems to occur at times in the year when the natural amount of light decreases, such as in the winter. Symptoms of SAD include hypersomnia, carbohydrate-craving and weight gain, as well as panic disorders and other ailments. In such cases, it has been found to be effective to apply light therapy, that is, to introduce the body to artificial light of varying intensities and wavelengths and at different times of the day, in order to increase the amount of light provided to the body. See, e.g., "Winter Depression, and Phototherapy", Gysin F.; Gross F. Acta Med Port (Portugal) December 1997, 10 (12) p 887–93.

Other types of non-seasonal, major depressive disorders, such as bulimia, have also been found to respond favorably to the application of various types of artificial light to supplement the natural light to the body of the subject. See, e.g., "Light Therapy in Bulimia Nervosa," Blouin A. G. et al., Department of Psychiatry, Ottawa Civic Hospital, Ontario, Canada. Psychiatry Res (Ireland) Feb. 28, 1996, 60(1) p 1–9.

Humans have an intrinsic body clock that responds to light cues to aid in synchronizing activities to the rising and setting of the sun. This phenomenon is referred to as the circadian cycle or circadian clock and is known to control a variety of physiological processes, including daily fluctuations in body temperature, hormone production, and even sleep itself.

The circadian cycle may become disoriented or confused, so that sleep-related disorders develop. For example, a person traveling through various time zones often has difficulty acclimating the circadian cycle to a new time zone that may be hours different from the previous time zone. This problem is commonly referred to as "jet lag" and usually is resolved in a few days. Other sleep-related disorders may be more chronic and very difficult to cure or overcome.

In such sleep disorder cases, it has also been determined that light therapy can be quite effective in helping the circadian cycle to adapt. In particular, research has indicated that light can be provided not only to the retina but to extraocular portions of the body to create a circadian response. U.S. Pat. No. 6,135,117 (Campbell et al.) discloses methods for providing nonocular light to the body to treat circadian rhythm problems and various sleep disorders. Campbell indicates that the delivery of extraocular light stimulus to certain regions, such as the popliteal region, can mediate and shift the phase of a circadian cycle. U.S. Pat. No. 6,164,787 (Seki) discloses an apparatus positioned beneath an airplane seat for administering light to the popliteal region to affect the circadian cycle during extended flights.

In the Campbell et al. patent, light was delivered using large fiber-optic light pads designed to treat jaundice in newborns. These pads were attached to a bulky power supply. In the Seki patent, light was administered by fixed apparatus disposed beneath the airplane seat connected to a halogen lamp in a vented metal housing having a fan attached thereto. Neither system lends itself to portability.

Seasonal affective disorder (SAD) and other mood disorders, as well as circadian disorders and other sleep problems, require periodic timed treatment given at precise times over a period of several days or weeks. During and between treatment times, the subject needs to be free to move about and take care of normal activities. In particular, the treatment of circadian problems presupposes that the subject is treated before, during or after sleep and/or travel.

Accordingly, it is important that the treating device be easily portable and, optionally, wearable so that the subject is able to carry out normal activities during treatment. Moreover, the nature of the treatment requires that a power supply be included, which must also be portable and wearable. In addition, the time intervals and intensity of treatment may vary widely, depending on the subject and the type and severity of disorder. Accordingly, a portable control device may also be needed for effective treatment. A wearable unit may be useful for providing periodic treatment of varying times and intensities while not causing substantial discomfort or interfering with the mobility of the subject.

It has also been determined that some wavelengths of light are more effective in treating certain disorders than others. Thus, treatment using light with a single wavelength or a plurality of wavelengths within a fairly small range is often preferred. Accordingly, a means for light delivery is needed that can provide monochromatic light focused on the desired light wavelength or range of light wavelengths needed to treat a particular disorder.

SUMMARY OF THE INVENTION

The present invention involves providing light to areas of the body where there are substantial blood vessels near the surface of the skin, so that the light can interact with photoactive substances in the blood to correct various problems. An effective area for the administration of light has been found to be the popliteal region, the area directly behind the knee joint, because there are many blood vessels close to the surface of the skin. Other effective regions for contacting blood vessels are the chest, neck, arms and abdominal area.

The present invention comprises novel apparatus and methods for delivering light to regions of the body having substantial blood vessels near the surface of the skin. The apparatus is a portable, wearable device having a light source and a battery pack. The light source is a plurality of light-emitting diodes (LEDs) capable of emitting light having a single wavelength or range of wavelengths within a desired wavelength range. A controller may be included to activate the light source for preselected times and durations.

In one embodiment, a portable light-emitting device is provided for delivering light to the blood supply of a human body through an exposed nonocular area of skin on the body. The device includes an attachment for wearing the device on a portion of the human body. A portable light delivery unit is connected to the attachment for providing light to the blood supply through the skin of the portion of the human body. A portable power supply is connected to the light-emitting device for powering the light-emitting unit.

In another embodiment, the portable light delivery unit is an LED array having a single wavelength or range of wavelengths. The LED array is also preferably selected to deliver light within a predetermined circular angle over a specific portion of the skin of the human body.

In another embodiment of the present invention, a portable controller is associated with the light delivery unit to control the times and durations of light delivery to the blood supply of the human body. The controller is also preferably programmable to vary the light delivery to the body. A portable programming device is preferably also attached to the controller to change the programming in the controller.

In another embodiment of the present invention, the portable light delivery unit includes a plurality of small light strips, each strip having a plurality of LEDs thereon for delivering light through the skin to the blood supply of the body. Preferably, the LEDs of each strip are electrically connected together to coordinate the light delivery to the body.

In another embodiment, a method is provided for delivering light to the blood supply of a human body through an exposed nonocular area of skin on the body. The method includes attaching a portable light delivery unit to a portion of the human body, providing light to the blood supply through the skin of the portion of the human body by means of the portable light delivery unit, and providing power to the portable light delivery unit by means of a portable power supply connected to the portable light delivery unit. The method includes delivery of the light by means of a portable LED array.

Another method of the present invention involves delivery of light to a portion of the body having a substantial amount of blood vessels near the surface of the skin, such as the popliteal area of the knee or the abdominal area of the body. The method may include selection of the angle at which the light is provided to the exposed area of the skin and/or the intensity of the light provided to the exposed area of the skin. The method may further involve controlling the timing and duration of the light delivery to the exposed area of skin. The methods of the present invention may be used to treat various bodily problems, including seasonal affective disorders, depression and mood disorders, circadian rhythm problems and various types of sleep disorders.

Accordingly, the present invention has many features, including providing a portable light delivery system using a monochromatic LED array. This system of the present invention has the advantages of delivering desirable wavelengths and intensities of light, wearability because the unit is portable and compact, being battery powered, which assists in portability, low heat output adding to comfort of use, and long life. The LED unit may be flexible to conform to the shape of the body part, so as to enhance the wearability of the device.

Moreover, the portability and wearability of the device of the present invention enables applying light to areas that have many blood vessels near the surface of the skin, such as the back side of the knee, where there is optimal contact with the bloodstream to receive the light rays. These advantages and improvements and others will be shown by reference to the following detailed description of preferred embodiments of the invention with reference to the attached drawings.

DETAILED DESCRIPTION

The novel light delivery apparatus of the present invention has a number of features and advantages, including a light delivery apparatus that is portable, wearable, and programmable and has the capability of delivering light energy at wavelengths within a preselected wavelength range and at or above a preselected light intensity. It is important that the device be portable and wearable for the reasons previously stated—namely that the subject needs treatment over an extended period for multiple time periods and preferably while the subject is mobile and able to accomplish necessary tasks. The wearability of the apparatus is also enhanced by the use of thin substrates connected together to form a flexible light treatment apparatus.

Wearability is particularly important in delivering light to the popliteal region or other suitable regions of the body, since the patient is likely to be mobile and involved in numerous activities. In addition, light is intended to be delivered to the subject at certain preselected periods during sleep or daily activities, so it may be securable to the body. In addition, the light delivery apparatus may be comfortable and non-obtrusive to allow the subject to sleep and move comfortably during treatment.

In some instances, it may be important that the light delivery device be programmable, so that the subject can receive treatment while asleep or while preoccupied with other matters. Obviously, one cannot expect the subject to be awakened for treatment when a critical element of that treatment involves administering light during a specific period of the sleep cycle.

The Apparatus

Figure 1:
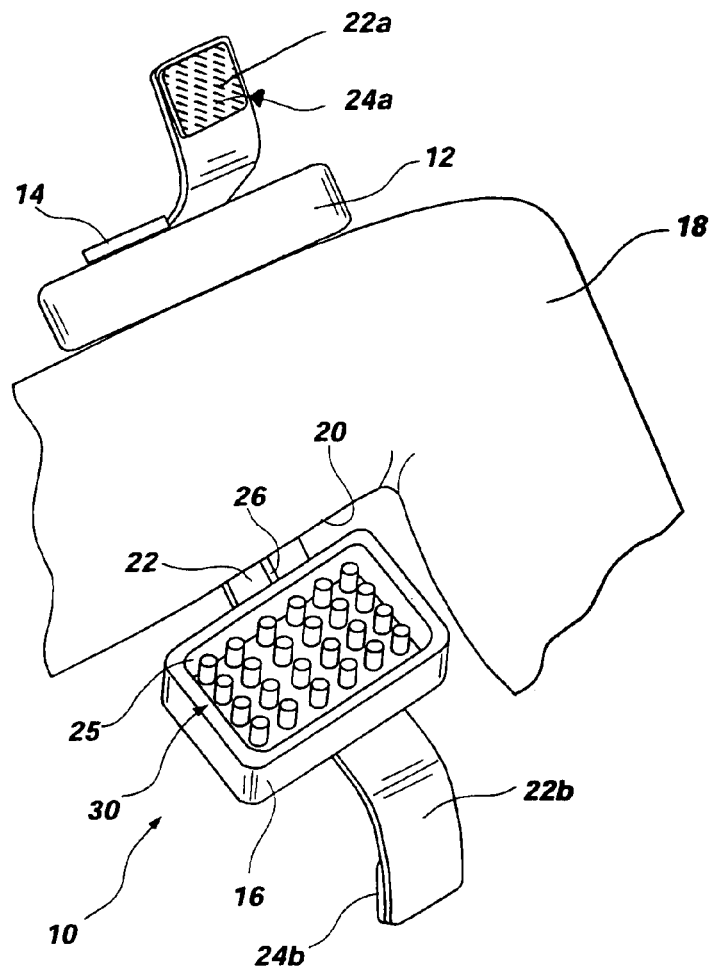
FIG. 1 is a perspective, schematic view of one embodiment of the light delivery apparatus of the present invention.
Figure 2:
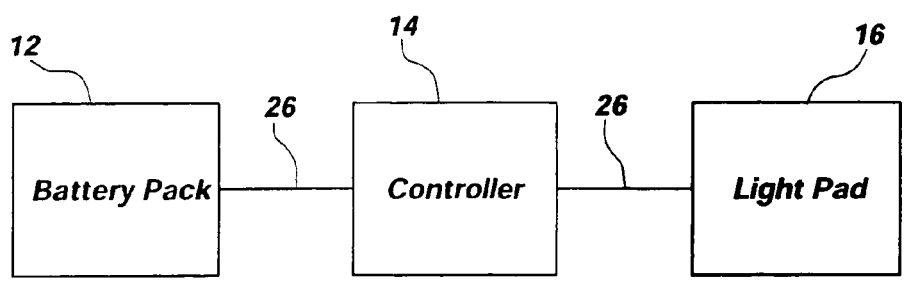
FIG. 2 is a block diagram of the components of the light delivery apparatus of FIG. 1.

Referring now to FIGS. 1 and 2, one embodiment of the light treatment apparatus of the present invention is shown generally at 10. The apparatus includes a battery pack 12, a controller 14, and a light pad 16. Light treatment apparatus 10 may be secured to the subject's leg just above and/or below the knee 18 and, more particularly, with light pad 16 in juxtaposition to the popliteal region 20. Alternately, the light pad 16 may be applied to other body regions discussed earlier where numerous blood vessels are near the surface of the skin.

A strap 22 having strap ends 22a and 22b with VEL-CRO™ pads 24a and 24b or other attachment or connection elements thereon, which may be formed from a hook and loop fastener (e.g., VELCRO®), may be used to adjustably and releasably mount light treatment apparatus 10 to knee 18 with light pad 16 placed against popliteal region 20. Alternatively, a light treatment apparatus 10 according to the present invention may include a single-piece strap, which may be expandable and/or contractible (e.g., elastic).

Battery pack 12 is preferably any suitable conventional battery pack having sufficient electrical energy storage capacity to support illumination of light pad 16 for the treatment times selected on controller 14. A wire 26, which may be embedded in strap 22, otherwise carried thereby, or separate from strap 22, delivers this electrical energy from battery pack 12 to light pad 16. In the present embodiment, battery pack 12 is shown separate from light pad 16, although both elements could be integrated into a single structural unit and provide the same benefits.

In the present embodiment, with the battery pack 12 and light pad 16 as separate elements, controller 14 is mounted on the battery pack 12 (as shown) so that it is readily accessible to the operator while the light pad 16 is in position on the popliteal region 20 behind knee 18. The separation of battery pack 12 and light pad 16 is also advantageous, in that only the light pad 16 needs to be positioned behind the knee 18 for extended light delivery treatment (up to three hours), particularly during sleep times. Therefore, the bulk behind the knee 18 is minimized and the comfort of the subject is enhanced.

In one embodiment, controller 14 is a conventional device that activates the light pad 16 at a given intensity for as long as it is turned on by connecting the battery pack 12 or by a simple on-off switch. Another embodiment of the controller 14, discussed later, includes a conventional programming device (not shown), such as input keys, to provide the desired program for the controller 14 to follow. Alternately, the programming device may be separated from the light delivery apparatus to minimize the weight and bulk to be carried by the patient. In such case, the programmer could be a separate device that would only be attached at certain rest periods so as to change the programming of the controller 14, as desired.

In another embodiment, the controller 14 may be replaced by an on-off switch or entirely omitted from the system, so that the light pad 16 is operational for as long as it is engaged with the battery pack 12. In this usage, the subject follows a program of his own choosing or as prescribed by a professional to apply light to the desired area.

Light pad 16 is shown having a recess 25 with a plurality of LEDs 30 mounted therein. The depth of recess 25 is coordinated with the height of LEDs 30, so that the upper ends of LEDs 30 are essentially flush with or slightly recessed relative to the upper surface of light pad 16. In this manner, light pad 16 and, more particularly, LEDs 30 are all placed in direct contact with popliteal region 20. Since none of the LEDs 30 extends above the upper surface of light pad 16, no undue pressure points are provided that could otherwise interfere with the circulatory integrity and comfort of popliteal region 20.

Figure 3:
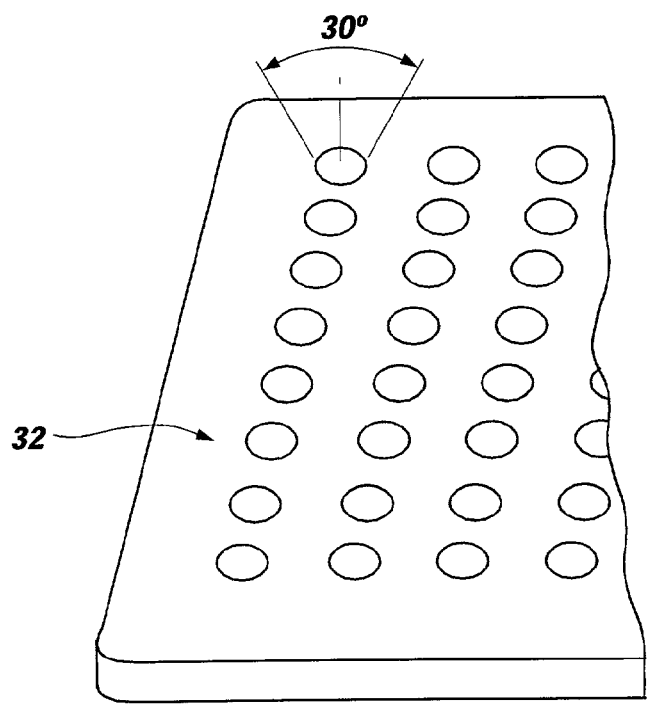
FIGS. 3 and 4 are schematic views showing different angles of illumination for LED arrays according to preferred embodiments of the present invention.
Figure 4:
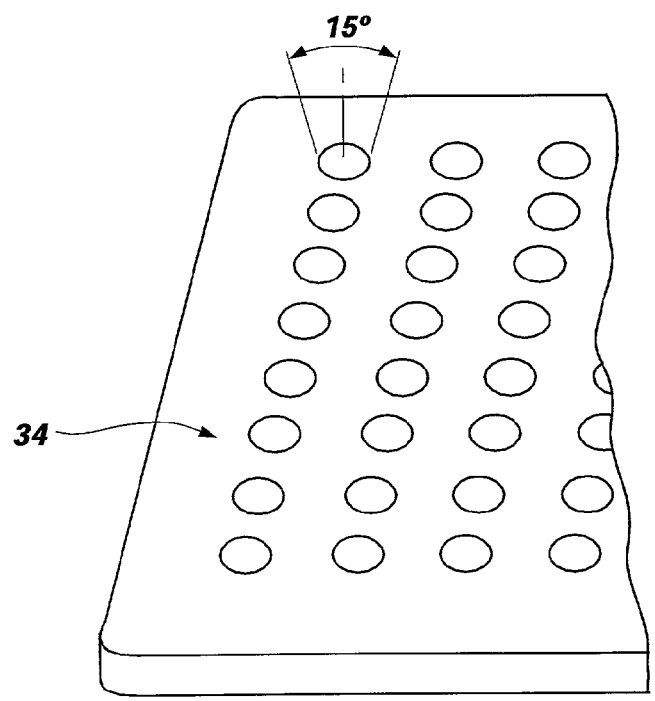

FIGS. 3 and 4 show different preferred embodiments using LEDs with different angles of illumination. In FIG. 3, an array of LEDs 32 provides an angle of illumination of about 30°, considered a relatively broad diffusion of light. Using this type of LED array, the light delivery will be more diffuse to cover a greater area, but is not likely to have as much intensity as more focused light delivery. The light delivery system is likely to function better where there is an abundance of blood vessels relatively close to the surface of the skin. In that situation, it would be advantageous to deliver light to a broad area with less need for light penetration.

Conversely, in FIG. 4, an array of LEDs 34 provides an angle of illumination of about 15°. This approach results in greater intensity and less diffusion of the light delivery system. Thus, this type of LED is most effective where there are not as many blood vessels near the surface of the skin and greater light penetration is needed.

In one example, 15° LEDs 34 shown in FIG. 4 were used driven by a current of about 20 milliamps. The LEDs 34 each provided monochromatic light having a wavelength of about 465 nanometers and an intensity of about three milliwatts per square centimeter at a temperature of about 104° Fahrenheit. This provided more heat than acceptable to be worn for any extended period. Accordingly, the forward current was reduced to about five milliamps. The resulting intensity was reduced to about two milliwatts per square centimeter at a temperature of about 93° Fahrenheit, which provided acceptable penetration and comfort level.

In a second example, 30° LEDs 32 shown in FIG. 3 were used having monochromatic light at a wavelength of about 465 nanometers. Again, the forward voltage may be provided at a current of about 20 milliamps. The resulting intensity was about three milliwatts per square centimeter at a temperature of about 103° Fahrenheit. Again, this heat was beyond the comfort zone. The forward current was reduced to about 10 milliamps. The resulting intensity was about two milliwatts per square centimeter at a temperature of about 94° Fahrenheit, which provided acceptable penetration and comfort level. This adjustment brought the temperature down to a comfortable level for the wearer.

For light delivery to the popliteal region, the 30° LEDs 32 were found to be preferable because they covered a greater area with the same intensity and about the same temperature. In delivering light to other nonocular regions, the 15° LEDs 34 may be more suitable, because of the possibility of greater light penetration.

Another advantage of using an LED array is that a specific light frequency and wavelength can be selected that is advantageous for each application. In the present preferred embodiment for delivering light to the popliteal region, it was found that light having a wavelength of about 490 nanometers was effective in shifting circadian cycles. In applying light to the popliteal region for the treatment of seasonal affective disorder and mood disorders, light having a wavelength of about 474 nanometers was found to be effective. In treating jaundice, light having a wavelength of about 460 nanometers was found to be effective. All wavelengths mentioned above include a wavelength range of plus or minus fifteen percent (15%).

Figure 5:
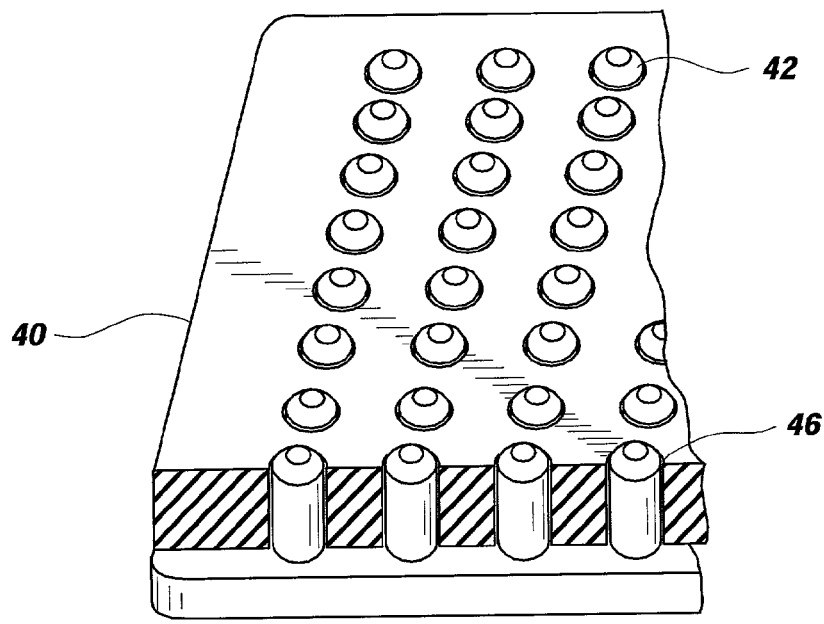
FIG. 5 is a schematic view showing an embodiment having padding around the LED array of the present invention.

Referring now to FIG. 5, padding 40 is shown secured around LED array 42. The padding 40 extends around the periphery of the LED array 42. Preferably the padding 40 also extends over the surface of LED array 42, with openings 46 to enable the LED array 42 to direct light to the skin surface.

Figure 6:
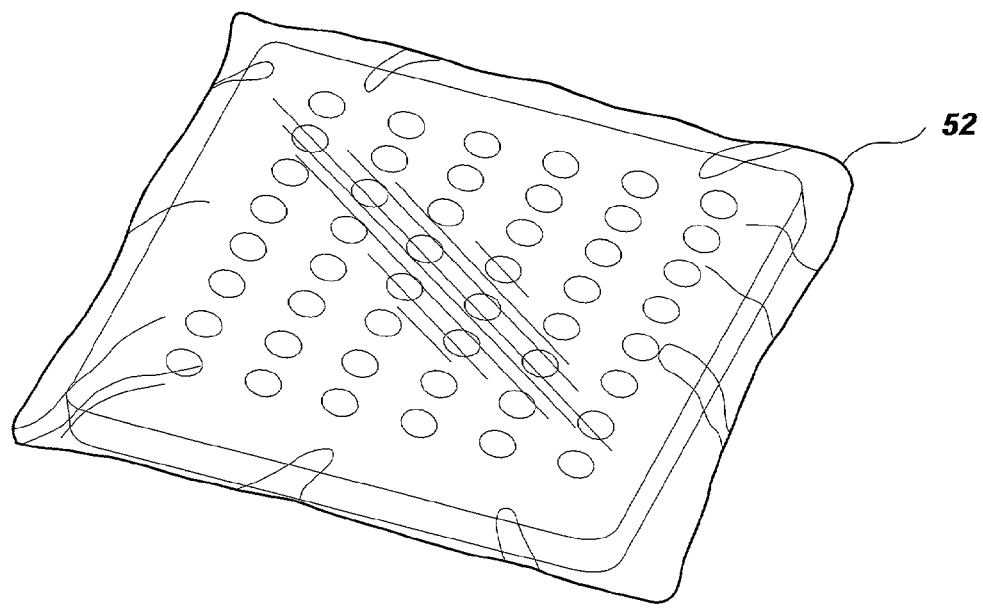
FIG. 6 is a schematic view showing an embodiment having waterproof sealing around the LED array of the present invention.

FIG. 6 shows an embodiment of the light delivery apparatus of the present invention, in which the LED array is completely encapsulated in a waterproof material 52. This waterproof material 52 may be of any suitable material, such as plastic, and is likely to be thicker for light delivery to the popliteal region at the back of the knee than for devices where light delivery is provided to some other regions of the body.

The portable battery pack 12 may be of any suitable size and power. The size may be minimized to enhance portability, while still being large enough to deliver the necessary power for the LED array. In the present invention, conventional nickel cadmium rechargeable battery units having an output of about 12 volts and a capacity of either about 300 milliamps*hours or about 700 milliamps*hours may be used, depending on the desired results.

Figure 7:
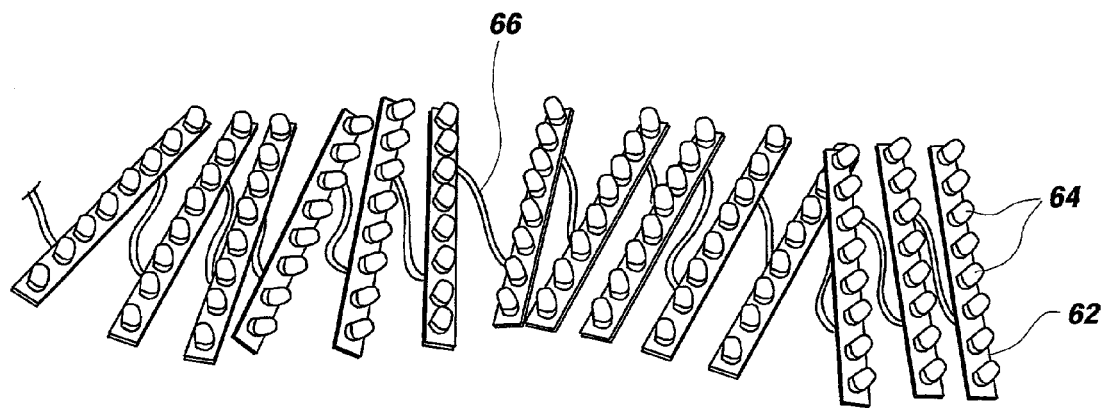
FIGS. 7 and 8 are schematic views showing another embodiment of the light pad for the light delivery apparatus of the present invention.
Figure 8:
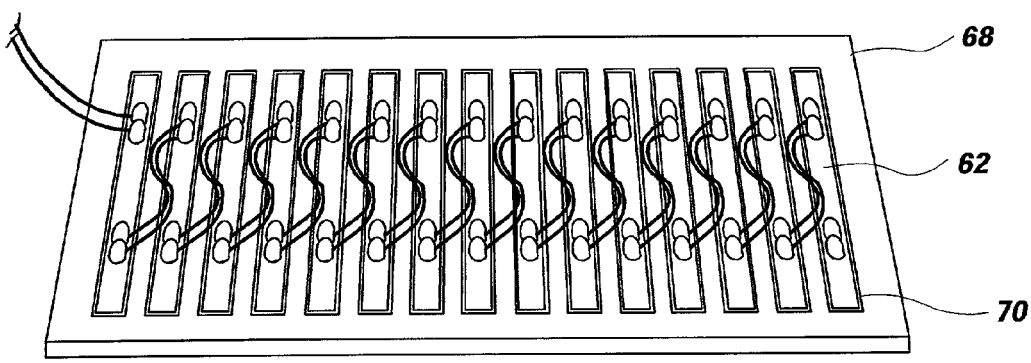

Referring now to FIGS. 7 and 8, an alternate embodiment is shown for the light pad 16 shown in FIG. 1 for the light delivery system of the present invention. As shown in FIG. 7, each of a plurality of light strips 62 has several LED units 64 spaced from each other in a row on each strip. The LED units 64 on each light strip 62 are electrically connected together. Wires 66 connect the LED units 64 of each light strip 62 to the LED units 64 of the adjoining strips. Light Strips 62 are preferably made of suitable short and narrow strips of substrate material, such as a fabric, plastic, rubber, or foam rubber material, so that the pad can easily bend to conform to the surface of the body portion, such as the underside of the knee, the neck or other suitable body part.

FIG. 8 shows the back side of a pad 68 with the light strips 62 mounted therein. Preferably, spaced-apart cavities 70 are formed in the pad 68 and sized to accept the light strips 62. The cavities 70 include holes on the front side thereof (not shown) for the LED units 64 to direct light out of the front of the pad 68, similar to the padding 40 around LED array 42, shown in FIG. 5.

Figure 9:
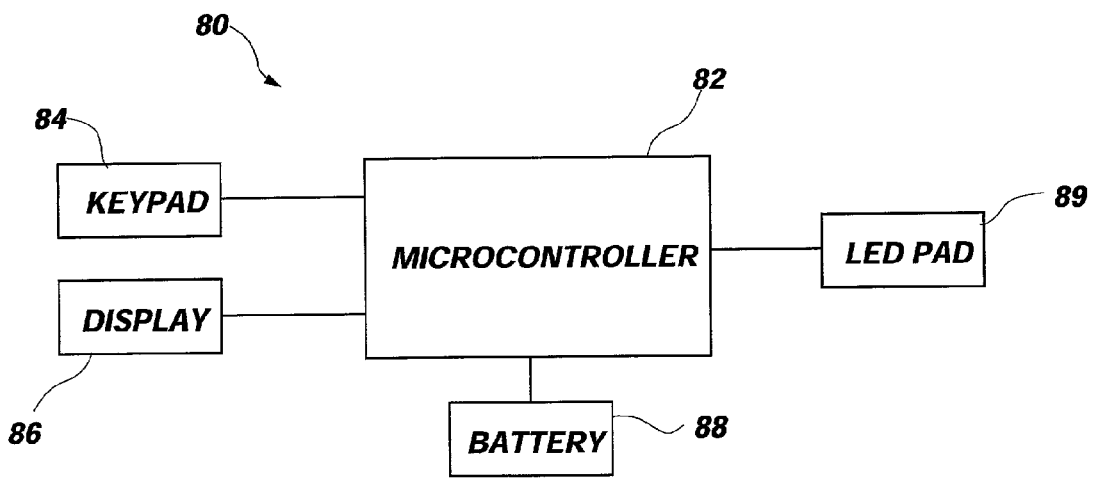
FIG. 9 is a block diagram showing an embodiment of the controller shown in FIG. 1.

With reference now to FIG. 9, the components of one preferred embodiment of a system 80 according to the present invention are shown. In this embodiment, system 80 includes a microcontroller 82 connected to programming devices, such as keypad 84 and display 86, which may be used to control and communicate with microcontroller 82 which, in turn, operates LED pad 89 in a desired manner. A power source 88, such as the depicted battery pack, may be included in system 80 so as to provide power to one or more of microcontroller 82 and display 86. Selected data are periodically input via keypad 84 to program microcontroller 82 in the operation of LED pad 89.

Figure 10:
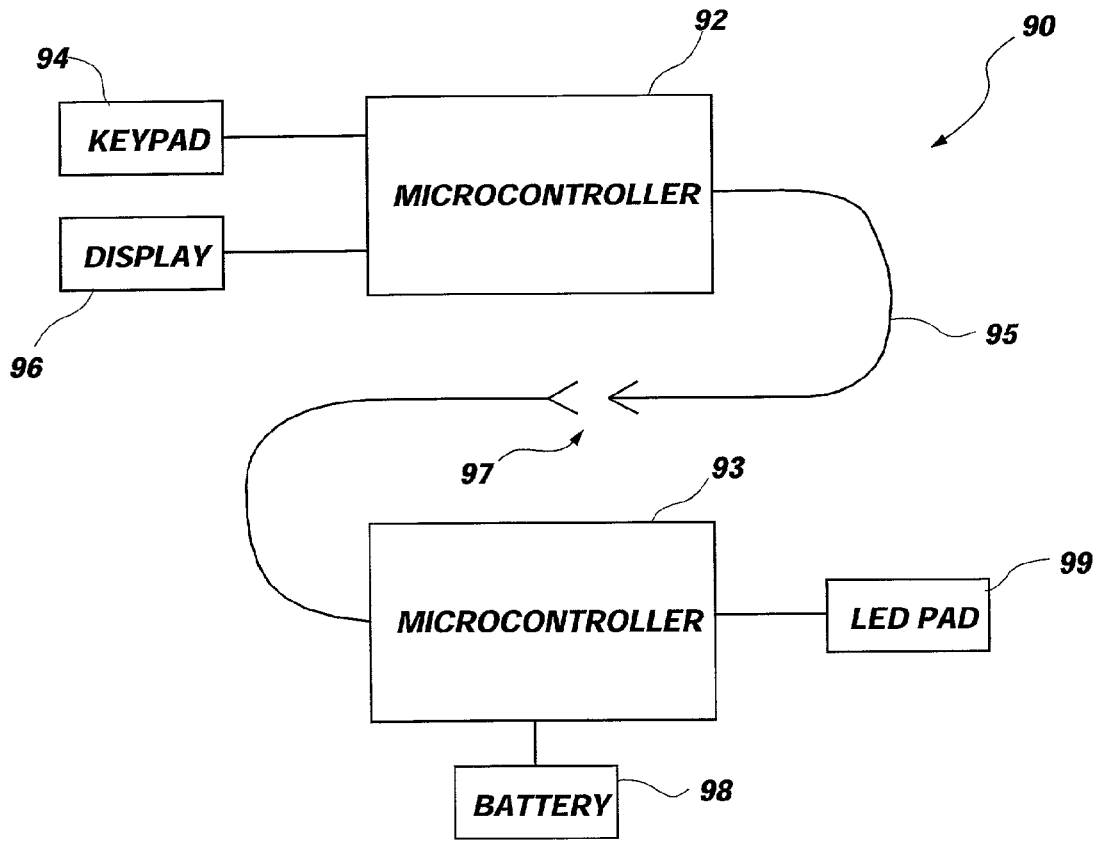
FIG. 10 is a block diagram showing an alternate embodiment of the controller shown in FIG. 1.

An alternative system 90 is shown in FIG. 10, in which the programming function is provided by a microcontroller 92 that is separate from a second microcontroller 93 that operates the LED light pad 99. As shown, the programming devices, keypad 94 and display 96, are connected to a microcontroller 92 that is separate from the LED pad 99 and battery 98, in order to reduce the bulk of the light delivery device worn by the subject. Microcontroller 92 may, for example, be linked to a second microcontroller 93 via a data cable 95 and socket and plug link 97. Second Microcontroller 93 receives the programming via data cable 95 and operates the LED pad 99 accordingly.

In this embodiment, the microcontroller 92, keypad 94 and display 96 do not have to be portable, so the size and weight of the portable device worn by the subject are minimized. Instead, microcontroller 92 may be connected periodically to the second microcontroller 93 at any convenient time, such as during bedtime, to input new programming. Microcontrollers 82, 92 and 93 are conventional microcontrollers that can be readily obtained in the industry. One example is microcontroller, model number PIC 16F873, made by Microchip Technology in Chandler, Ariz.

Operation of the Apparatus

An example of the operation of the embodiment of the present invention shown in FIG. 1 is as follows. The light treatment apparatus 10 is positioned so that light pad 16 is placed against popliteal region 20 in a manner that LEDs 30 deliver light directly against the tissue of popliteal region 20. Battery pack 12 with controller 14 mounted thereon, as well as light pad 16, are secured to the knee 18 by strap 22. Strap ends 22a and 22b are secured together by joining VELCRO™ pad 24a to VELCRO™ pad 24b.

Apparatus 10 is used by simply activating the controller 14 with power from the battery pack 12, which in turn enables the light pad 16 to provide light to the subject as long as the system is operational. Alternately, if the controller 14 is not present, the subject activates the light pad 16 by simply connecting it to the battery pack 12 for the prescribed periods of time. The entire system is portable and is worn by the subject who can go about his or her activities during the time that light is applied to the blood supply of the subject. The subject may be instructed to wear the unit for selected times over one or more days to achieve the desired result.

Similarly, the embodiment shown in FIG. 9 which is entirely portable and wearable by the subject, includes a microcontroller 82 that may be programmed at will by keypad 84 and display 86 to activate the LED pad 89. Alternately, as shown in FIG. 10, the microcontroller 92, key pad 94 and display 96 may be left in the subject's room or elsewhere for periodically updating the portable second microcontroller 93. Data cable 95 may also include battery wires (not shown) for recharging battery 98 at the same time that second microcontroller 93 is receiving new programming.

In one example of operation, keypad 84 and display 86 may be used to set the current time in microcontroller 82. The same input means may also be used to provide microcontroller 82 with the time that the LED pad 89 is to be turned off and the duration of time the LED pad 89 should remain on. Several such cycles of on and off time can also be input to microcontroller 82.

With the system 90 shown in FIG. 10, the same data may be input to microcontroller 92, which then calculates the appropriate on and off times. This information is then fed to second microcontroller 93 at a convenient time so that second microcontroller 93 can operate the on and off time of LED pad 99 accordingly.

One example of a light delivery treatment schedule for a flight from New York City to Paris is as follows: (1) the day before travel, light is provided from 5:00 a.m. to 6:00 a.m. New York City time; (2) on the day of travel, light is provided from 3:00 a.m. to 4:00 a.m. New York City time; and (3) on the first day in Paris, light is provided from 8:00 a.m. to 9 a.m. Paris time.

As a further embodiment of the present invention, microcontroller 82 or the combination of microcontrollers 92 and 93 may be programmed to process the corresponding LED light pads through duty cycles, in which the light pads 16 are switched repeatedly on and off. Such duty cycles may have any combination of on and off times and may be set to operate at low frequencies or at higher frequencies of hundreds or thousands of cycles per second. This duty cycle operation enables the use of light of higher intensity than would ordinary be used without causing the buildup of heat that would be uncomfortable to the wearer. The use of more intense light enables deeper penetration of light to the body so that more effective treatment may be achieved in certain cases where greater light intensity is needed.

For instance, in the preceding example, if a higher intensity of light is desired to achieve deeper penetration, one may apply the more intense light in a duty cycle with equal on and off times, so that the light is effectively applied to the body only half of the time that the light pad 16 is turned on.

The periods during which the light is applied may be the same as in the above example, namely, one hour the day before travel, one hour during the day of travel and one hour during the day after travel, each at the indicated times. In this application, since the light intensity has been substantially increased, the use of a duty cycle lessens the total application of light so that there is no uncomfortable heat buildup. However, the reduction in the amount of light applied is compensated for by the increased intensity of light, enabling the desired treatment through deeper penetration.

Although the above embodiments are representative of the present invention, other embodiments will be apparent to those skilled in the art from a consideration of this specification and the appended claims, or from a practice of the embodiments of the disclosed invention. It is intended that the specification and embodiments therein be considered as exemplary only, with the present invention being defined by the claims and their equivalents.

What is claimed is:

1. A portable light-emitting device for delivering light to the blood supply of a human body of a subject through a nonocular area of skin on the human body, comprising:
   (a) an attachment for securing the light-emitting device to a portion of the human body;
   (b) a portable light delivery unit comprising an array including interconnected, elongate strips, each strip including a plurality of linearly arranged light sources, each light source providing focused light within a cone of light illumination having an angle of from about 15° to about 30°, the portable light delivery unit being connected to the attachment for providing light to the blood supply through skin of the portion of the human body; and
   (c) a portable power supply connected to the portable light delivery unit.

2. The portable light-emitting device of claim 1, wherein the array provides light having one or more wavelengths within a specifically determined range.

3. The portable light-emitting device of claim 1, wherein the portable light delivery unit provides light within a specifically determined range of light intensity.

4. The portable light-emitting device of claim 1, further comprising a pad on the attachment to provide a cushion between the portable light delivery unit and the human body.

5. The portable light-emitting device of claim 1, further comprising waterproofing material over the portable light delivery unit and the portable power supply.

6. The portable light-emitting device of claim 1, further comprising a portable controller unit for selectively controlling the portable light delivery unit.

7. The portable light-emitting device of claim 6, wherein the portable controller unit is programmable.

8. The portable light-emitting device of claim 7, wherein the portable controller unit includes a portable programming device on the portable light delivery unit to selectively input programming to the portable controller unit.

9. The portable light-emitting device of claim 7, wherein the portable controller unit comprises a linking device for connecting to a programming unit that is separate from the portable controller unit.

10. The portable light-emitting device of claim 9, wherein the portable power supply is rechargeable and wherein the linking device includes a device to connect to the portable power supply for recharging the portable power supply.

11. The portable light-emitting device of claim 6, wherein the portable controller unit includes a device to switch the portable light delivery unit off and on in multiple duty cycles during a time that light is provided to the blood supply.

12. The portable light-emitting device of claim 1, wherein the portable light delivery unit comprises a plurality of LED light units.

13. The portable light-emitting device of claim 1, wherein the light is delivered at an angle of about 15 degrees to the axis of emission.

14. The portable light-emitting device of claim 1, wherein the light is delivered at an angle of up to about 30 degrees to the axis of emission.

15. The portable light-emitting device of claim 1, wherein the array emits light having a wavelength in the range of about 460 nm to about 490 nm, inclusive.

16. A method of delivering light to the blood supply of a human body through a nonocular area of skin on the human body, comprising:
   (a) securing a portable light delivery unit to a portion of the human body;
   (b) providing focused light to the blood supply through skin of the portion of the human body by delivering an array of cones of light to an exposed area of skin, each cone having an angle of about 15° to about 30° to an axis of emission of the focused light; and
   (c) providing power to the portable light delivery unit by means of a portable power supply connected to the portable light delivery unit.

17. The method of claim 16, wherein the light is provided by a portable array having one or more wavelengths within a specified range.

18. The method of claim 16, wherein the light is provided to a knee of the human body.

19. The method of claim 16, wherein the light is provided to an abdominal area of the human body.

20. The method of claim 16, wherein the light is provided to a neck area of the human body.

21. The method of claim 16, wherein the light is provided to an arm area of the human body.

22. The method of the claim 16, wherein the light is provided by facial area of the human body.

23. The method of claim 16, further comprising attaching a portable controller to the portable light delivery unit.

24. The method of claim 23, further comprising controlling an amount of time during which the light is provided to the skin of the portion of the human body.

25. The method of claim 23, further comprising controlling an intensity of the light provided to the skin of the portion of the human body.

26. The method of claim 23, further comprising attaching a portable programming device to the portable controller.

27. The method of claim 26, further comprising selectively programming the portable controller to deliver light body at selected times and intensities.

28. The method of the claim 16, wherein the portable light delivery unit delivers light in multiple duty cycles wherein the light is repeatedly turned on and off during a period that light is delivered to the blood supply.

29. The method of the claim 16, wherein the light is provided by the portable light delivery unit to the blood supply of the body to treat seasonal affective disorder.

30. The method of claim 16, wherein the light is provided by the portable light delivery unit to the blood supply of the human body to treat mood disorders.

31. The method of claim 16, wherein the light is provided by the portable light delivery unit to the blood supply of the human body to treat circadian rhythm sleep disorders.

32. The method of claim 16, wherein light is provided to the blood supply through the skin at or within an angle of about 15 degrees from an axis of a corresponding light source of the array.

33. The method of claim 16, wherein light is provided to the blood supply through the skin at or within an angle of about 30 degrees from an axis of a corresponding light source of the array.

34. The method of claim 16, wherein light having a wavelength in the range of about 460 nm to about 490 nm, inclusive, is provided to the blood supply through the skin.

35. A method of delivering light to the blood supply of a human body through a nonocular area of skin on the body, comprising:

(a) enveloping a portable light delivery unit within a watertight container;
(b) securing the portable light delivery unit to a portion of the human body;
(c) providing power to the portable light delivery unit by means of a portable power supply connected to the portable light delivery unit; and
(d) providing focused light in multiple duty cycles to the blood supply by delivering light to an exposed area of the skin of the portion of the human body in illumination cones having angles of about 15° to about 30° by means of the portable light delivery unit.

* * * * *